United States Patent

Meyer

[11] Patent Number: 5,831,763
[45] Date of Patent: *Nov. 3, 1998

[54] HOLDER FOR HIGH RESOLUTION SAMPLE IMAGING

[75] Inventor: Robert D. Meyer, Houston, Tex.

[73] Assignee: Meyer Instruments Inc., Houston, Tex.

[ * ] Notice: The term of this patent shall not extend beyond the expiration date of Pat. No. 5,612,819.

[21] Appl. No.: 816,506

[22] Filed: Mar. 13, 1997

Related U.S. Application Data

[63] Continuation-in-part of Ser. No. 493,964, Jun. 23, 1995, Pat. No. 5,612,819.

[51] Int. Cl.$^6$ ............................ G02B 21/26; G02B 21/06
[52] U.S. Cl. ........................ 359/391; 359/385; 359/390
[58] Field of Search ................................. 359/363, 368, 359/391–398; 356/244

[56] References Cited

U.S. PATENT DOCUMENTS

| | | | |
|---|---|---|---|
| 4,159,875 | 7/1979 | Hauser | 359/396 |
| 4,674,846 | 6/1987 | Lippman | 359/398 |
| 4,974,094 | 11/1990 | Morito | 359/385 |
| 5,062,697 | 11/1991 | Mitchell | 359/391 |
| 5,249,077 | 9/1993 | Laronga et al. | 359/385 |
| 5,325,232 | 6/1994 | Lahcanski et al. | 359/391 |
| 5,612,819 | 3/1997 | Meyer | 359/391 |

*Primary Examiner*—Thong Nguyen
*Attorney, Agent, or Firm*—Bush, Riddle & Jackson

[57] ABSTRACT

A system to obtain a high resolution image of a relatively large sample (11) for viewing by a researcher includes a rectangular holder (20) that receives a microscope slide (10) and which includes a glass filter (40) that reduces the amount of illumination of the sample without reducing the Kelvin light temperature, and a scanner (22) that receives the holder (20) and produces electrical signals which are fed to the hard drive of a computer (23) where a high resolution image of the sample is displayed on the monitor (24). One embodiment of the invention (FIGS. 5–8) utilizes a separate high intensity light source (60A) for the scanner (22A) for illuminating opposed surfaces of the slide (10A), and a fiber optic light pipe (66A) connects the high intensity light source to the holder (20A) within the scanner (22A).

6 Claims, 2 Drawing Sheets

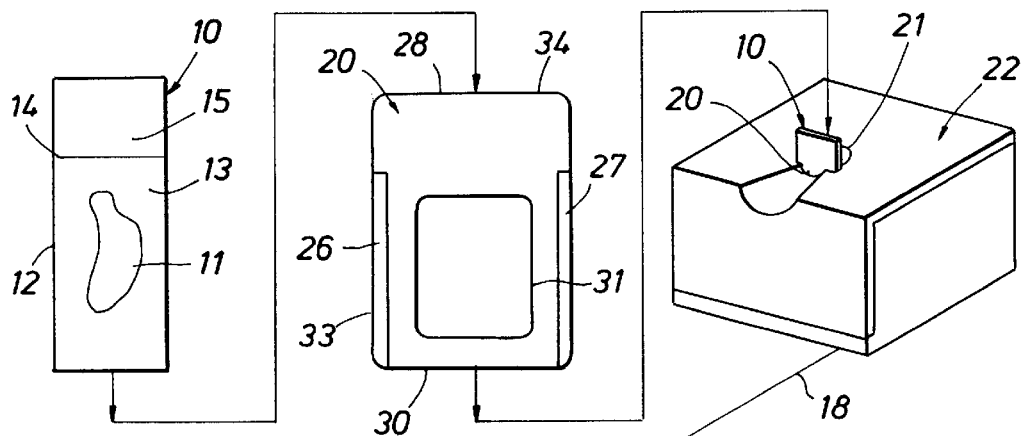
FIG. 1
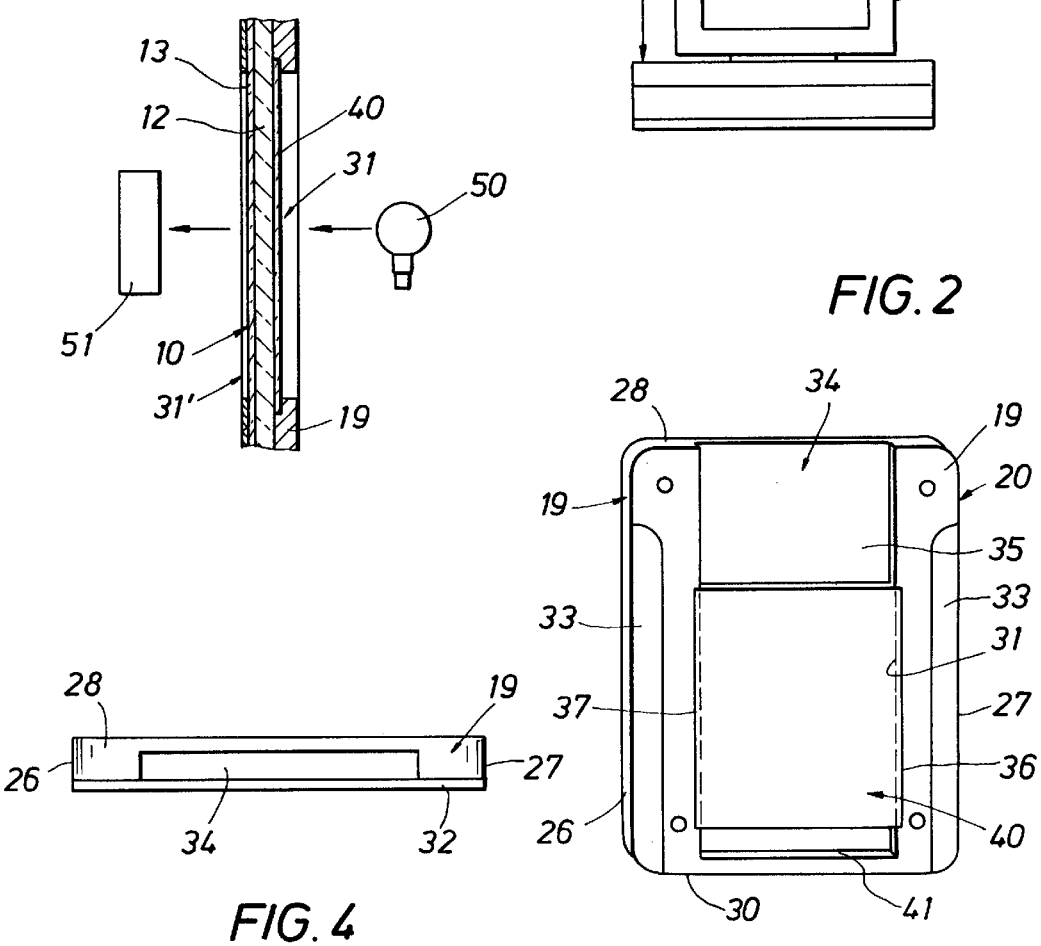

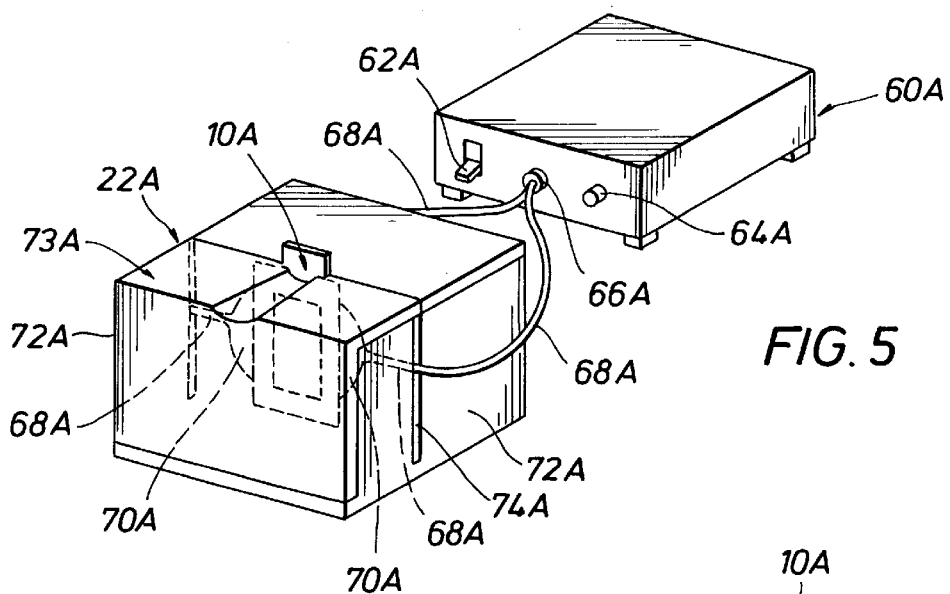
FIG. 5
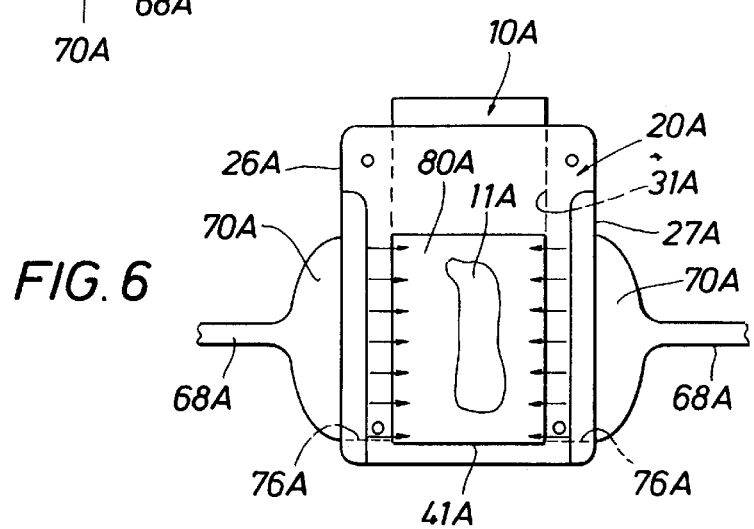
FIG. 6
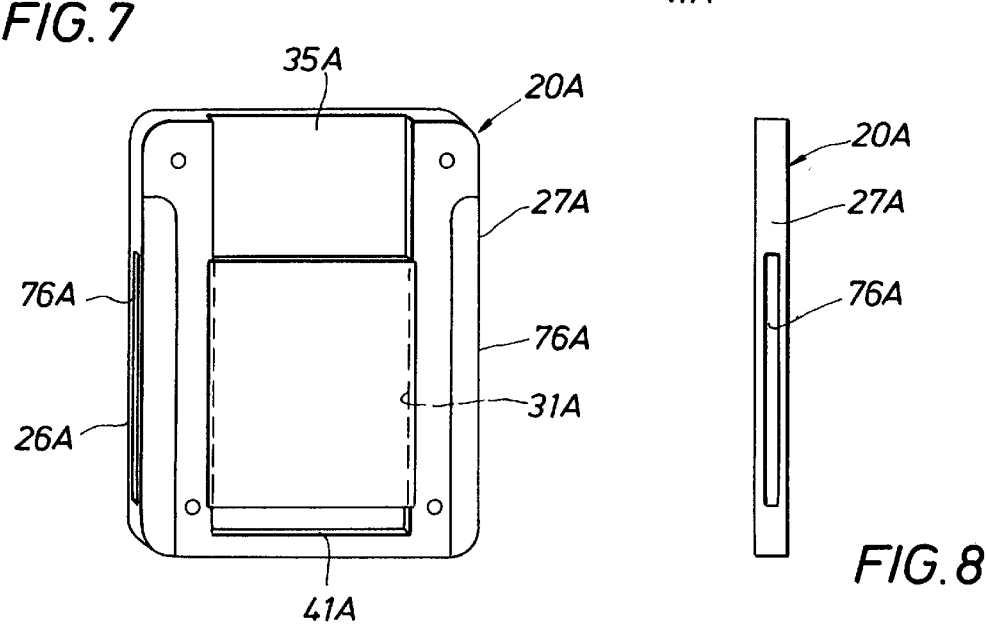
FIG. 7
FIG. 8

HOLDER FOR HIGH RESOLUTION SAMPLE IMAGING

CROSS REFERENCE TO RELATED APPLICATION

This application is a continuation in part of application Ser. No. 081493,964 filed Jun. 23, 1995, now U.S. Pat. No. 5,612,819.

FIELD OF THE INVENTION

This invention relates generally to the imaging of samples such as those used in research work in the field of medicine, and particularly to new and improved high resolution imaging of relatively large samples mounted in slides.

BACKGROUND OF THE INVENTION

A conventional practice in this field is to attach a video camera to a microscope, in order to generate signals that are representative of an image in the field of view of the microscope. Such signals are fed to a computer having a capture card (frame grabber), and the resultant image is displayed on the monitor. The display on the monitor typically has a resolution in the order of 640 by 480 pixels, provided the resolution of the camera is equal to or greater than this value. When using modern laboratory microscope at a low power objective such as $1x_1 2.5x_1 4x_1$ the field of view, which is circular, ranges from about 20 mm to 5 mm, although certain more expensive research instruments can have a field of view in the order of 28 mm to 7 mm. When a video camera is attached to the microscope the field of view decreases to about 10 mm to 2.5 mm, since the camera will have a rectangular field of view with an aspect ratio of 4 to 3. Thus the largest rectangular field of view that a typical video camera can display when attached to a microscope is about 10 mm×7.5 mm. This severely limits the size of the largest tissue sample image that can be viewed on a monitor to such size, namely 10mm×7.5 mm.

Moreover, a typical laboratory microscope video camera and display system is very expensive, and can cost in the range of from $10,000–$15,000 or more, excluding the cost of the microscope. To obtain larger fields of view and higher capture and display resolutions, the above-mentioned research microscopes can be used with additional intermediate lenses and higher performance capture and display electronics. However such systems cost tens of thousands of dollars more than the typical systems.

Microscope specimen slides that are viewed through a microscope usually are made of glass and commonly are rectangular having side dimensions of 1 in.×3 in. The thickness dimension is 1.1 mm. A sample of histological tissue is prepared and sliced to a very thin section (3 to 5 microns), which is mounted on the glass slide and protected by a rectangular coverslip that has dimensions of 40 mm long×20 mm wide×0.15 mm thick. The coverslip limits the size of the largest tissue sample that can be mounted. Such slides are viewed by pathologists, anatomists and biologists and the like on a daily, routine basis. Indeed literally millions of such slides are created and viewed by thousands of researchers and clinicians every day, so that improvements in accordance with this invention have wide application in the art.

As noted above, where the size of the tissue sample exceeds 10 mm×7.5 mm, the use of a microscope and video camera to capture and display an image thereof has an inherent, very serious problem. Even though the specimen slide and coverslip can accommodate a fairly large tissue sample section, for example up to 40 mm×24 mm, there is no way when using conventional technology to display the entire sample section for viewing by the clinician. Of course as a practical matter, the side dimensions of a 35 mm photographic slide do not exceed 36 mm ×24 mm.

It is an object of the present invention to provide a new and improved imaging system that enables display of relatively large samples at high resolution.

Another object of the present invention is to provide a new and improved imaging system that employs a scanner and a unique slide holder that enables display of the entirety of a large tissue sample with high resolution.

A further object of the invention is to provide such a system in which a separate high intensity light source is transmitted to the slide holder for illuminating opposed sides of the slide to permit visual observation of unstained samples.

SUMMARY OF THE INVENTION

These and other objects are attained in accordance with the concepts of the present invention through the provision of a unique slide holder apparatus that is dimensioned to be received in the receptacle of an electronic scanner having a charge-coupled array that can scan a slide such as a 35 mm photographic slide and provide a high resolution image thereof. The output of the scanner is fed to a computer which generates a display on a computer monitor. The holder apparatus has front and rear walls that define a viewing window. A piece of filter glass is retained between the walls on the outer side of the holder apparatus, such glass being optically flat, clear, and of neutral density. The flat characteristic prevents distortion, and the glass has no discernable impurities, i.e. is clear. The neutral density characteristic means that the Kelvin temperature of light passing through it is not affected, however it is preferred that the amount of light be reduced by about 40%. A pocket is formed through one end of the holder and between the filter glass and the rear wall thereof. Such pocket has width, thickness and length dimensions such that the tissue sample slide with its coverslip can be inserted therein from such end and, when fully seated, a sufficient length of the slide remains exposed beyond the end wall of the holder apparatus to enable its insertion and withdrawal with the fingers. When positioned in the scanner receiver, the CCD array of the scanner can scan the entire slide and its large tissue sample at a high rate with extremely high resolution and provide an accurate replication of the information in the slide. The display can have a resolution as high as 2700×3900 pixels. The image is in color, or black and white, can be of entire sections of glands and arteries and the like, and is accomplished in a quick and economical manner.

1 embodiment of the invention utilizes a separate high intensity light source transmitted by a fiber optic light pipe or cable to the holder for the slide to provide illumination of opposed sides of the slide. Such an illumination produces a darkfield image which has a black background to permit visual observation of unstained samples, such as unstained histological samples. Autoradiological techniques are normally employed with unstained tissue samples.

BRIEF DESCRIPTION OF THE DRAWINGS

The present invention has the above as well as other objects, features and advantages which will become more clearly apparent in connection with the following detailed description of the invention taken in conjunction with the appended drawings in which:

FIG. 1 is a schematic diagram of the overall imaging system of the present invention;

FIG. 2 is a fragmentary, schematic side sectional view of the holder of the present invention with slide positioned therein;

FIG. 3 is a front isometric view of the holder apparatus with thickness exaggerated for purposes of clarity and with the metal cover removed;

FIG. 4 is an enlarged top view of the holder apparatus;

FIG. 5 is a perspective of another embodiment of the present invention in which a separate high intensity light source is provided for the holder on illuminate opposed sides of the specimen slide;

FIG. 6 is a front elevation of the holder showing a fiber optic light pipe from the light source connected to the holder on opposed sides of the specimen slide;

FIG. 7 is a front elevation of the holder shown in FIG. 6 with the fiber optic light pipe removed; and FIG. 8 is a side elevation of the holder shown in FIG. 7.

DESCRIPTION OF THE INVENTION

Embodiment of FIGS. 1–4

Referring initially to FIGS. 1–4 in which a preferred embodiment of the invention is shown on FIGS. 1–4, a specimen slide 10 mounts a very thin section of tissue 11, which as shown can be a longitudinal section of an entire infant mouse. The slide 10 includes a rectangular piece of glass 12 having the tissue section 11 mounted thereon and covered by a thin coverslip layer 13 which extends up to a level 14. The region 15 above the level 14 provides space to adhere an identification sticker, and for handling the slide with the fingers. The tissue sample 11 can be most anything of interest to a diagnostician or clinician, and can be relatively large in size. For example, the entire section of a human gonad gland, ovary, artery or vein can be readily mounted in the slide 10. The slide 10 fits into a holder 20 that is constructed in accordance with the present invention. The structural details of the holder 20 will be described below. The holder 20 is sized and arranged to be received in the receptacle 21 of a 35 mm photographic slide scanner 22 that contains a charge-coupled scanning array of sensors that allows the entire viewing area of a 36 mm×24 mm color slide to be scanned at 2700 dpi in approximately one (1) minute. The scanner 22 is commercially available as the "SprintScan" 35 scanner from Polaroid Corp. Electrical signals from the scanner 22 are fed by a cable 18 to a computer 23 and displayed on its monitor 24. A color, or black and white, print can be made on a printer (not shown) if desired.

The holder 20 is generally rectangular in shape and has elongated side walls 26, 27 and relatively shorter top and bottom walls 28, 30. A rectangular viewing window 31 is formed through the body 19 of the holder 20, and a slide receiving slot or pocket 35 that is formed within the body extends through an opening 34 in the top wall 28 and down past the lower edge of the window 31. Although numerous materials could be used to make the body 19 of the holder 20, one preferred construction employs polished aluminum. The front wall of the body 19 can be recessed to a shallow depth except along a portion 33 of each side as shown, and a thin metal cover plate 32 as shown in FIG. 4 that is attached by screws or the like (not shown) closes the front of the body. A window 31' (FIG. 3) corresponding to rectangular window 31 formed in body 19 is formed through the back wall of the body 19.

As shown in more detail in FIG. 2, the edges 36, 37 which define the sides of the slot 35 are recessed to a slightly wider and deeper dimension in order to receive and retain a rectangular glass filter 40. The filter 40 is carefully made to be optically flat and clear so as not to introduce any distortion or aberration in color, and to have a neutral density so that the Kelvin temperature of light passing therethrough is not affected. The filter 40 does, however, reduce the amount of light passing through by about 40%.

The thin metal plate 32 body 19 in FIG. 2, when mounted on the body 19, traps the side edges of the filter 40 in the recessed edges 36 and 37 of the slot 35. When the specimen slide 10 is inserted through the opening 34 and advanced fully downward in the slot 35 until its lower end surface rests on bottom wall 41, the sample 11 will appear in the window 31 while the top portion 15 extends well above the top wall 28 so that it can be grasped by the fingers for insertion and removal. FIG. 3 is a fragmentary cross-section which shows the slide assembly 10 positioned in the slot 35 with a specimen sandwiched between the glass 12 and the thin piece of coverslip 13 and positioned in the window 31. A suitable light source such as a fluorescent device 50 which puts out daylight white light at a Kelvin temperature of about 56000° shines through the filter glass 40 and illuminates the specimen in the slide 10. The CCD array 51 in the scanner 22 scans the entire area of the window 31 at a resolution of 2700×3900 pixels and produces signals which are fed directly to the hard drive of the computer 23. A very high resolution color image of the tissue sample 11 is obtained, and the sample size can be as large as 36 mm×24 mm.

OPERATION

In operation and use, a thin slice or section of tissue 11 is mounted on the glass 12 of the slide 10, and the section is covered by the coverslip 13. Then the slide 10 is positioned in the holder 20 by inserting it down into the slot or pocket 35. When properly positioned, the tissue 11 is framed by the window 31 while the top portion 15 remains above the upper wall surface 28. The holder 20, which has approximately the same width and thickness dimensions as a 35 mm photographic slide, then is positioned in the receptacle 21 of the scanner 22 with the filter 40 on the outer side, or toward the light source 50 in the scanner. Light from the florescent source 50 passes through the window 31, the filter glass 40, the slide glass 12 and the window 31' and illuminates the section 11 which is scanned by the CCD array 51 to create a high resolution color image thereof. Due to the large size of the windows 31 and 31', the image scanned can be as large as 36 mm×24 mm, which allows the imaging of entire brain sections of certain research animals, human prostate and other glands, arteries, or any other microscopically large section in a quick and economical manner. The system of the present invention eliminates the need for a low power microscope-video camera imaging system, and provides savings of thousands of dollars to an individual user.

Although the holder apparatus 20 has been described in connection with the orientation shown in the drawings, that is with the top thereof providing the opening into the slot 35, it will be recognized that the holder could be loaded in another type of scanner in an orientation other than the vertical, or into the side of the scanner 22 in another orientation. Thus the use herein of phrases such as "top", and "bottom" are merely for purposes of convenience of illustration, and not in any limitative sense. It also is within the scope of the present invention for the holder apparatus 20 to already be positioned in the receptacle 20 when the slide 10 is inserted therein.

Embodiment of FIGS. 5–8

Another embodiment of the present invention is shown in FIG. 5–8 in which a separate high intensity light source generally shown at 60A in FIG. 5 is provided for attachment to the scanner 22A for illuminating the slide 10A retained by the holder 20A. Light source 60A is a fiber optic illuminator including a high intensity quartz halogen projection bulb, an on-off switch 62A, and a rheostat 64A. A fiber optic light pipe 66A extends from illuminator 60A and is bifurcated into two branches 68A for extending to opposite sides 72A of scanner 22A. Each fiber optic branch 68A has an end fiber optic bundle 70A. An outer protective sheath is provided for each branch 68A. A fiber optic illuminator which has been found to be satisfactory is sold under the name Intralux 6000 by Volpi Manufacturing, USA of Auburn, N.Y.

Each side of scanner 22A has an elongate slot 74A therein sized and arranged to receive fiber optic bundle 70A for insertion within scanner 22A for connection to holder 20A. Side walls 26A and 27A of holder 20A are formed with slots 76A that communicate with pocket 35A and rectangular viewing window 31A. Rectangular specimen slide 10A is received within pocket 35A and is supported on bottom 41A. Slots 76A are sized and arranged to receive fiber optic bundles 70A in a releasable press fit.

Operation of Embodiment of FIGS. 4–8

Slide 10A with the sample thereon is inserted within pocket 35A supported on bottom 41A. The fiber optic end bundles 70A on fiber optic pipe 66A from fiber optic illuminator 60A are inserted within slots 74A of opposed sides 72A of scanner 22A. Bundles 70A have an outer molded fitting which is press fitted within slots 76A of holder 20A. A front cover 73A may be pivoted to an open position to permit insertion of holder 20A. Illuminator 60A is energized and light flows from bundles 70A from the edges of slide 10A along opposed front and back sides of slide 10A and the sample 11A thereon to create a darkfield image which defines a black background 80A about sample 11A. With a darkfield illumination, unstained samples, such as histological samples, may be visually observed. Various autoradiological techniques utilize unstained tissue samples. Except as indicated above, the operation of the embodiment of FIGS. 5–8 is similar to the operation of the embodiment of FIGS. 1∝4. Scanner 22A normally has a florescent bulb or device to provide light as shown in the embodiment of FIGS. 1–4. However, when the light source 60A is utilized in the embodiment of FIGS. 5–8, the light source within scanner 22A is deenergized and not used.

While the above embodiments are utilized primarily with color images and tissue samples, black and white images may be utilized and the samples may be other than tissue samples, such as plant cross sections or prepared rock samples or sections.

It now will be recognized that a new and improved system for providing a high resolution image of a relatively large sample has been disclosed. The term "sample" as used in the specification and claims herein shall be interpreted as including sections, specimens, and other materials that can be secured to a microscope slide. Since certain changes or modifications may be made in the disclosed embodiments without departing from the inventive concepts involved, it is the aim of the appended claims to cover all such changes and modifications falling within the true spirit and scope of the present invention.

What is claimed is:

1. A scanner assembly for use in enabling a microscope slide to be positioned in a photographic slide scanner having a slide-receiving receptacle, said scanner assembly comprising:

a holder having a generally rectangular housing sized and arranged to be received in said receptacle, said housing having front and rear wall surfaces and opposed end wall surfaces connecting said front and rear wall surfaces;

front and rear window means opening through said respective front and rear wall surfaces;

a generally rectangular slot formed in said housing and opening through one of said end wall surfaces to form a pocket arranged to receive said microscope slide in a manner such that a relatively large sample mounted therein in located in axial alignment with said front and rear window means;

said housing having opposed side wall surfaces positioned between said front and rear wall surfaces, each of said side wall surfaces having a light source slot therein in communication with said pocket; and a light source operatively connected to each of the light source slots to provide light to said pocket for illumination of said slide within said pocket.

2. A scanner assembly as set forth in claim 1 wherein:

said light source comprises a separate high intensity light source; and fiber optic cable means extend from said high intensity light source to said light source slots to provide light to said pocket and opposed surfaces of said slide.

3. A scanner assembly as set forth in claim 2 wherein said fiber optic cable means are releasably connected to said holder when said holder is received within said receptacle.

4. A scanner assembly as set forth in claim 1 wherein:

said scanner has a pair of opposed sides with slots therein in axial alignment with said light source slots in said holder to provide for transmission of said light source to said pocket through said axially aligned slots.

5. A scanner assembly as set forth in claim 1 wherein:

said light source slots are sized and arranged to provide light to opposed surfaces of said slide and said sample so that a darkfield image is produced about said sample.

6. A scanner assembly for use in enabling a microscope slide to be positioned in a photographic slide scanner having a slide-receiving receptacle, said scanner assembly comprising:

a holder having a generally rectangular housing sized and arranged to be received in said receptacle, said housing having front and rear wall surfaces and opposed end wall surfaces connecting said front and rear wall surfaces;

front and rear window means opening through said respective front and rear wall surfaces;

a sample slot formed in said housing and opening through one of said end wall surfaces to form a pocket arranged to receive said microscope slide in a manner such that a relatively large sample mounted therein located in axial alignment with said front and rear window means:

a light source slot in said housing positioned between said front and rear wall surfaces in communication with said pocket;

a high intensity light source operatively connected to said light source slot to provide light to said pocket for illumination of said slide within said pocket; and fiber optic cable means extending from said high intensity light source to said light source slot to provide light to said pocket and said slide.

\* \* \* \* \*